United States Patent [19]
Morejon

[11] Patent Number: 5,713,869
[45] Date of Patent: Feb. 3, 1998

[54] TROCAR ASSEMBLY

[76] Inventor: Orlando Morejon, 235 SW. 79th Ave., Miami, Fla. 33144

[21] Appl. No.: 400,602

[22] Filed: Mar. 8, 1995

[51] Int. Cl.$^6$ .......................... A61M 5/32; A61M 5/178
[52] U.S. Cl. .................. 604/174; 604/26; 604/42; 604/164; 604/165; 604/175; 604/178
[58] Field of Search ................... 604/164, 165, 604/174, 175, 178, 264

[56] References Cited

U.S. PATENT DOCUMENTS

| | | | |
|---|---|---|---|
| 4,637,814 | 1/1987 | Leiboff | 604/27 |
| 4,649,913 | 3/1987 | Watson | 604/174 X |
| 5,002,557 | 3/1991 | Hasson | 604/174 X |
| 5,176,697 | 1/1993 | Hasson et al. | 604/174 X |
| 5,437,645 | 8/1995 | Urban et al. | 604/165 |

*Primary Examiner*—Robert A. Hafer
*Assistant Examiner*—Robert V. Racunas
*Attorney, Agent, or Firm*—Malloy & Malloy, P.A.

[57] ABSTRACT

An improved trocar assembly including an elongate shaft, with an open proximal end, an open distal end, an axial channel, and a substantially smooth exterior surface so as to prevent frictional engagement of the exterior surface with various tissue plains at an incision opening in the patient, and a distal expandable component, disposed substantially at the distal end of the elongate shaft and having at least one inflatable cuff structured to selectively maintain the elongate shaft partially within the patient subsequent to its insertion into the patient. Further, the inflatable cuff is preferably formed of a substantially non-elastic material such that a wall thickness thereof will be uniform along its entire surface both when it is in an inflated and uninflated orientation, thereby substantially reducing a likelihood that the inflatable cuff will rupture, while allowing the inflatable cuff to seal-off the incision opening about the elongate shaft to prevent airflow from an interior of the patient through the incision opening. Additionally, an upper collar assembly is slideably disposed on the elongate shaft and is structured to be locked in place along the elongate shaft so as to substantially captivate the various tissue plains of the patient between the upper collar assembly and the inflatable cuff, in its inflated state.

11 Claims, 5 Drawing Sheets

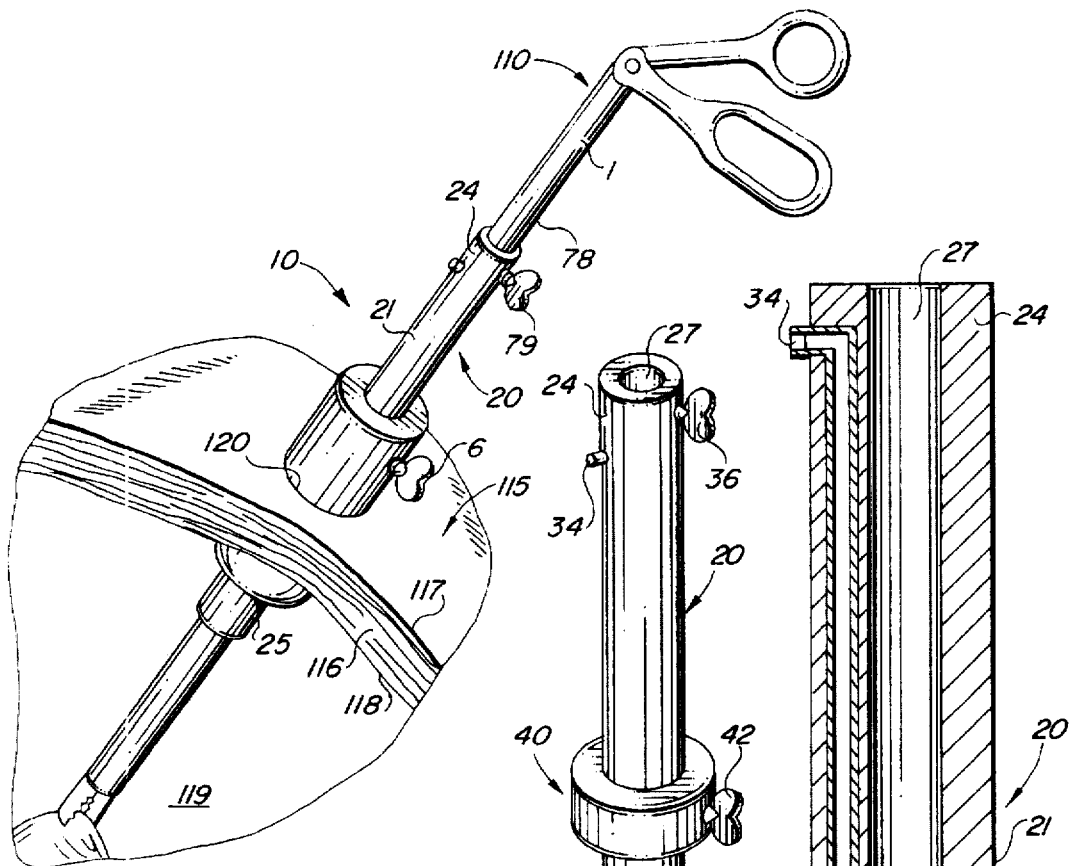
FIG. 1
FIG. 2
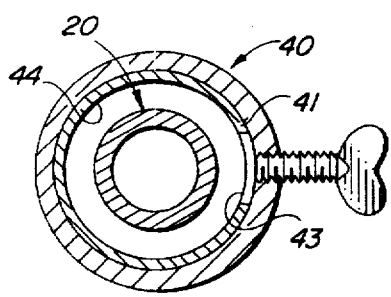
FIG. 4A
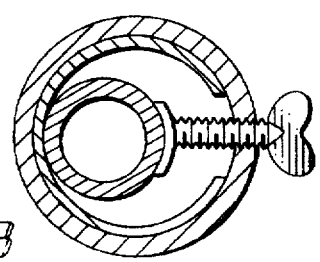
FIG. 4B
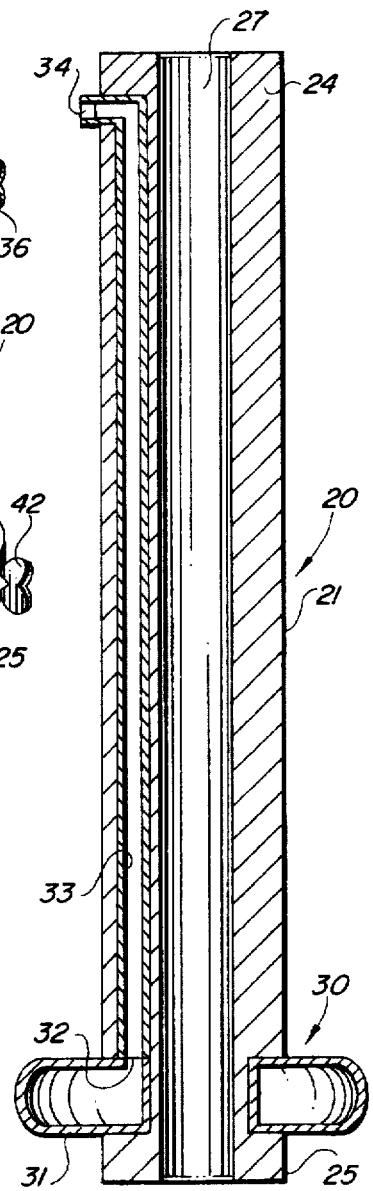
FIG. 3

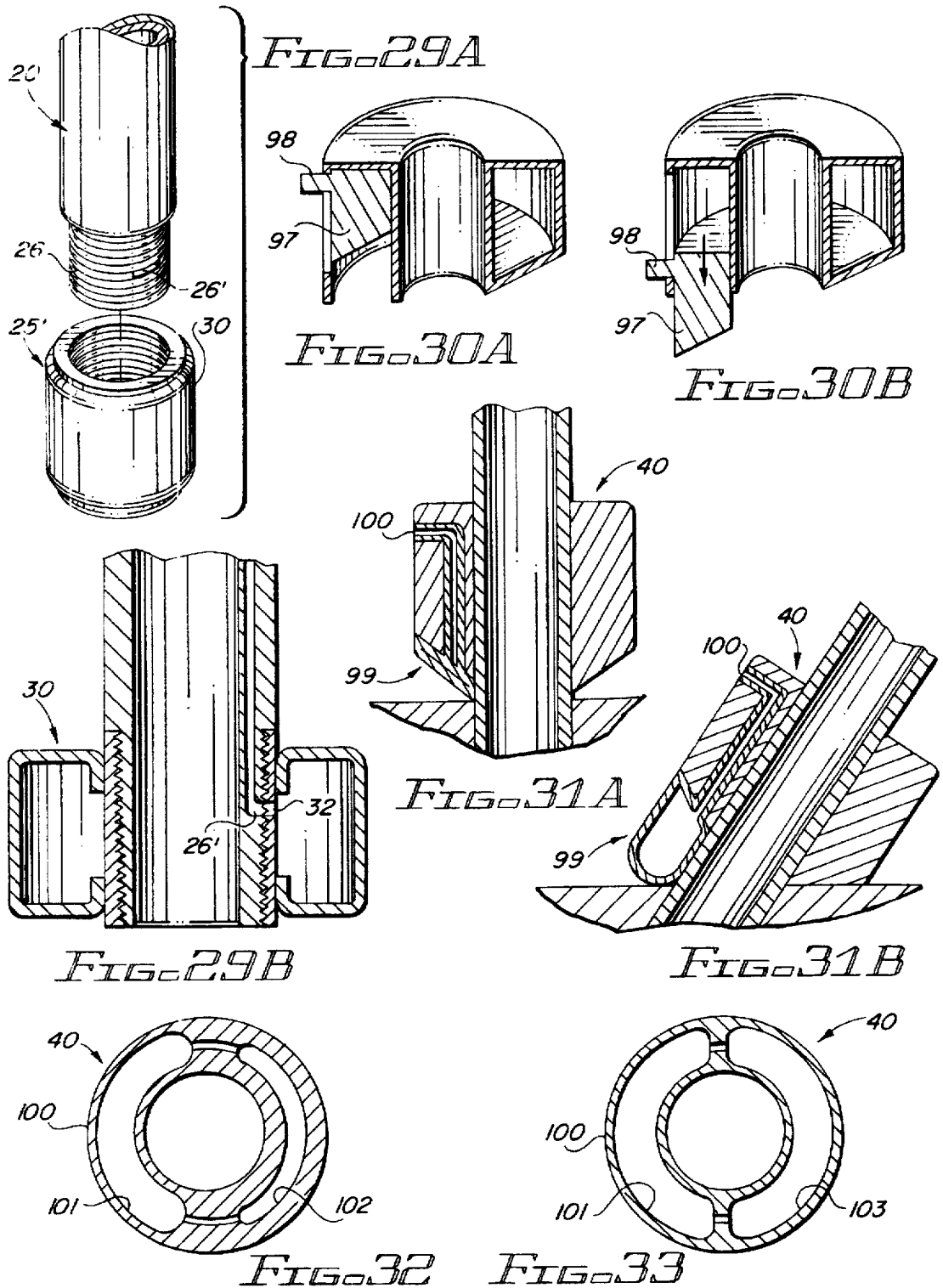

TROCAR ASSEMBLY

BACKGROUND OF THE INVENTION

1. Field of the Invention

The present invention relates to an improved trocar assembly structured to facilitate minimally traumatic insertion thereof into a patient, and provide for convenient, secure positioning into an effectively adjustable and maneuverable orientation, with minimal risk of interior rupture, while maintaining an effective seal of an insufflated peritoneal cavity.

2. Description of the Related Art

Trocar assemblies are frequently implemented, highly effective devices that are used in most minimally invasive surgical procedures. In particular, conventional trocar assemblies are commonly employed to maintain substantially small incisions within a patient while providing for the facilitated passage of surgical instruments therethrough in order to conduct various laparoscopic procedures. In use, a removable or retractable piercing end is included and used to enable the trocar to puncture the abdominal wall of the patient, thereby essentially creating a port into the patient. Through that port an instrument, a camera, a light, and various other items are inserted into the patient for the performance of the necessary procedure.

Presently, a variety of different trocar designs exist for use during laparoscopic surgical procedures and other forms of minimally invasive surgery. These numerous trocar designs vary primarily in their length, size, feel, method of introduction, and the method used to maintain pneumoperitoneum in the patient when an instrument is not present in the trocar. While these devices are generally effective to maintain pneumoperitoneum, maintain the incision open, and allow passage of an instrument therethrough, none employ a safe and effective means of stabilizing the trocar at the insertion site, a feature that would be substantially effective and beneficial to assist a surgeon in performing the various procedures in a safe and efficient manner. Similarily, none of the devices of the prior art provide for effective, maneuverable, stabilization and maintenance of the instrument disposed within the trocar in a desired position or orientation, and at a desired depth within the patient.

Accordingly, some trocar devices have been developed in an attempt to provide an effective method of stabilizing the trocar itself at the insertion site. For example, some have attempted to apply an adhesive disc to the skin surface around the insertion site for attachment to the trocar. In use, however, the adhesive disc tends to become dislodged during the course of the operative procedures due to the forces exerted thereon when maneuvering the instrumentation within the patient and due to moisture build-up between the adhesive surface of the disc and the underlying skin. Also, some designs have gone so far as to provide a pair of flanged arms that extend from the trocar body such that a doctor can suture the trocar to the patient, wrapping the suture around the arms for stability. Naturally, such a procedure causes a significant degree of unnecessary traumatization to the patient and are susceptible to being torn off of the patient.

Additionally, some alternative methods of trocar stabilization which have been developed incorporate a threaded exterior surface or sleeve which enables the trocar to be screwed into the patient's fascia at the insertion site so as to provide stabilization by engaging the various tissue planes at the insertion opening. This method, however, requires substantial further traumatization of tissues in order to create the threaded path, and can place underlying organs at great risk because of the significant, added downward force that may be necessary to introduce the trocar to an appropriate depth through the fascia.

Further, the conventional trocar assemblies of the prior art, including those which attempt to incorporate some means to secure the trocar within the patient, will generally not function to effectively seal the space between the trocar's outer perimeter and an internal surface of the incision opening, thereby resulting in air leaks. These air leaks around the trocar can result in a loss of pneumoperitoneum, along with losses of operative exposure and working space within the patient. Also, trocar use along with abdominal insufflation, which provides increased outward pressure within the abdomen, can result in slippage of the trocar tip out of the pneumoperitoneum, and accordingly can lead to air leakage into the subcutaneous tissue resulting in the development of subcutaneous emphysema. As such, in an attempt to prevent dislodgement, there is a tendency on behalf of a physician to place an excessive length of the trocar into the patient, a procedure which can not only be dangerous as a result of inadvertent damaging of internal organs, but which also severely limits the working length of the instrument that extends through the trocar.

In an attempt to solve some of the problems exhibited by the prior art, the references to Allgood (U.S. Pat. No. 5,122,122), Freitas et al. (U.S. Pat. No. 5,232,451), and Castillenti (U.S. Pat. No. 5,147,316) provide for clamped engagement with the peritoneal wall. Turning first to the related devices of Allgood and Freitas et al., in a preferred embodiment, they provide a dual sleeve design including an inner trocar sleeve surrounded by an outer sleeve that retains a mushroom hinge which expands within the patient, upon retraction of the outer sleeve, to prevent the trocar from exiting the patient while the mushroom hinge is expanded. This outer sleeve, however, adds an unnecessary circumferential layer to the trocar sleeve and thereby necessitates an incision opening of a larger size. Such a larger incision opening can be hazardous to the patient as it is more likely to require fascial closure, an added procedure which can significantly increase operation time, and is more likely to lead to complications such as an abdominal wall hernia. Further, the inner cylindrical sleeve is not radiolucent and will therefore obstruct radiographic visualization of any underline anatomy.

As to the mushroom hinge, which is intended to keep the device stabilized relative to the abdominal wall, due to its rigid construction gaps are present between the individual hinge elements thereby making the structure substantially susceptible to pneumoperitoneal leaks. Additionally, the rigid hinge is also susceptible to pneumoperitoneal leaks that can occur at the sides of the trocar incision when the trocar is tilted during instrumentation. Accordingly, in an alternative embodiment of the Allgood and Freitas et al. devices, the mushroom hinge is replaced with an expandable sponge. This expandable sponge, however, also requires the external sleeve for compression and containment of the sponge until it has been inserted into the patient, may not provide a sufficiently rigid retaining surface, and can be susceptible to deterioration and possible fragmentation during retraction and release.

As a final alternative, the trocar devices of Allgood and Freitas et al. provide for an elastic inflatable balloon disposed at the distal end of the trocar. This inflatable, elastic balloon is structured to normally lie along an outer surface of the trocar and to expand in a balloon like manner upon inflation thereof. This balloon, however, while eliminating the need for an outer sleeve, can be substantially fragile and vulnerable to rupture. Specifically, the elevated internal and external pressures which affect the balloon, as well as the presence of various sharp instrumentalities and/or internal body masses can easily result in sudden, violent rupturing of the balloon, especially due to the high tension state in which the balloon is maintained. In particular, due to the nature of the balloon, as it is inflated it stretches and the material which comprises the exterior walls of the balloon becomes substantially thinner. Not only does the thinning of the walls make the balloon susceptible to rupture, but there is also considerable tension on the balloon wall. Further, the point at which the wall becomes thinnest is also the point of greatest tension, according to LaPlace's law of physics that defines the point of greatest tension as the point of greatest radius of the balloon, and the point which extends farthest from the trocar and is thus most susceptible to rupturing contact. Accordingly, it can be substantially hazardous to utilize such an inflatable balloon within the patient, especially due to the risk of balloon rupture that can lead to balloon fragmentation within the patient and possible abrupt dislodging and outward propulsion of the trocar which may or may not contain an instrument that is secured to an internal organ.

Additionally, the divides of Freitas et al. and Allgood incorporate exterior clamping mechanisms to provide for the engaging of the abdominal wall. In one embodiment of the invention, a rubber gasket member is utilized. The rubber gasket member is structured to slide down the exterior of the trocar shaft into an engaged position atop the patient. The rubber gasket member, however, is not secured in place by any means other than the frictional tension provided by the resilient material of the gasket member. This can be particularly dangerous because during most operative procedures internal fluids are generally present at the incision site, thereby making the gasket member highly susceptible to inadvertent lubrication by the internal fluids and accordingly slippage along the shaft resulting in dislodging of the trocar from its clamped orientation.

In an alternative embodiment, therefore, the devices of Allgood and Freitas et al. provide for a threaded or ratcheted exterior perimeter of the trocar shaft. Such exterior ratcheting or threading is structured to provide for a more secure engagement of the upper member in place atop the abdominal wall, but can also lead to hazardous and possibly severe trauma during insertion. Specifically, during insertion the threads or ratcheted edges can be quite rough and/or sharp and have a serrating affect that can severely traumatize the internal tissue plains. Such additional traumatization of the internal tissue plains can lead to substantial future complications. Also, the additional traumatization can occur if the angled orientation of the trocar must be maneuvered within the patient, as further grating of the interior tissue planes can result. Further, the threads or ratchets provide a greater degree of resistance during insertion of the trocar into the patient, and therefore increases the risk that too much additional force will be applied such that the trocar will be over inserted into the patient to the point of engaging and possibly damaging an internal organ before the trocar can be pulled out to an appropriate depth.

Similarly, the device of Castillenti attempts to overcome some of the draw backs of the prior art. This device, however, also includes a racheted exterior sleeve that can lead to substantial added incision traumatization and insertion resistance. Additionally, the trocar of Castillenti includes an inflatable, elastic balloon within the patient which as previously recited, becomes highly susceptible to rupture and fragmentation during operative use of the trocar. Further, the device of Castillenti is structured with the balloon in fluid flow interconnection with a distensible bulb, which is normally utilized to inflate the balloon. Upon a degree of internal pressure being applied to the balloon, however, air within the balloon is susceptible to backing-up out into the distensible bulb, which expands to receive the expelled air, thereby reducing the secure hold maintained by the balloon.

Accordingly, there is still a substantial need in the art for a trocar assembly which will provide for facilitated, minimally resistive insertion into the patient and minimal tissue traumatization, while still enabling for effective and appropriate external securing of an outer collar atop the abdominal wall. There is also a need for a trocar device which incorporates a safe and effective means of securing the trocar in place relative to the abdominal wall, while substantially reducing the risk of air leaks from within the patient and minimizing the risks of internal rupture or internal traumatization of the patient's tissue.

Additionally, the devices of the prior art do not enable instruments utilized by the trocar to be effectively and appropriately maintained in a secure and desired orientation during a procedure, thereby freeing a physician or physician's assistant to perform further tasks during the operation. Also, devices of the prior art, which do seek to clampingly maintain the trocar secured to the abdominal wall do not provide for the escape of internal air which accidentally leaks into the incision opening around the trocar shaft, thereby directing such leaking air into the interior tissue plains which can lead to subcutaneous emphysema. Further, the devices of the prior art which attempt to secure the trocar in place do not provide for effective variable or stationary positioning of the trocar assembly in a specific desired orientation.

SUMMARY OF THE INVENTION

The present invention is directed to an improved laparoscopy trocar assembly to be utilized during laparoscopic and other minimally invasive procedures. The assembly of the present invention includes an elongate shaft having an open proximal end, an open distal end, and an axial channel extending therethrough from the distal end to the proximal end. Further, the elongate shaft includes a substantially smooth exterior surface so as to prevent frictional engagement of its exterior surface with various tissue plains at an incision opening formed by the trocar. Accordingly, the force required to insert the elongate shaft into the patient is reduced and local tissue maceration and traumatization at the tissue plains is minimized.

Positioned at the distal end of the elongate shaft is a distal expandable component. The distal expandable component is structured to selectively maintain the elongate shaft partially within the patient, subsequent to the insertion of the distal end of the shaft and the distal expandable component into the patient. In order for the distal expandable component to maintain the elongate shaft partially within the patient, it includes at least one inflatable cuff. This inflatable cuff is structured to be selectively disposed between an inflated and an uninflated state within the patient, the inflated state being utilized to maintain the elongate shaft partially within the patient. Additionally, the inflatable cuff is formed of a substantially non-elastic material such that a wall thickness of the inflatable cuff will be uniform along an entire surface thereof both when the cuff is in the uninflated and the inflated states. Accordingly, a likelihood that the inflatable cuff will rupture is a substantially reduced. Further, the inflatable cuff is positioned so as to seal-off the incision opening about the elongate shaft thereby preventing air leakage from an interior of the patient through the incision opening. The inflatable cuff is structured to be exteriorly inflated by inflation means once the inflatable cuff has been inserted into the patient along with the distal end of the elongate shaft.

To prevent the elongated shaft from sliding further into the patient, once the inflatable cuff has been inflated, an upper collar assembly is included. The upper collar assembly is slideably disposed on the elongated shaft substantially at a proximal end thereof. Further, the upper collar assembly includes locking means which engage the elongate shaft to non-slideably secure the collar assembly at a relative position along the substantially smooth exterior surface of the elongated shaft. Accordingly, the various tissue plains of the patient, which have been penetrated by the elongate shaft, will be substantially captivated between the upper collar assembly and the inflatable cuff. Additionally, the upper collar assembly is preferably structured to allow any air which does seek to exit the patient through the incision opening, about the exterior surface of the elongated shaft, to completely exit the patient, thereby substantially preventing internal air leaks into the various tissue plains, a circumstance that can lead to subcutaneous emphysema.

Finally, the trocar assembly includes introduction means structured and disposed to facilitate introduction of the elongate shaft through the various tissue plains of the patient so as to form the incision opening.

It is an object of the present invention to provide an improved laparoscopy trocar which can be stably and securely maintained in a patient so as to facilitate the insertion of operative instruments therethrough.

Another object of the present invention is to provide an improved trocar assembly which can be secured in a patient, which will not substantially resist insertion thereof into the patient, and which will not result in unnecessary traumatization or maceration of the various tissue plains at an incision opening.

Yet another object of the present invention is to provide an improved trocar assembly which can independently maintain an instrument inserted into a patient therethrough in a secure, desired orientation.

A further object of the present invention is to provide a trocar assembly which provides a user with substantially maneuverability for the use of an operative instrument inserted therethrough.

An additional object of the present invention is to provide an improved trocar assembly which will not trap air that may leak through the incision opening, about the elongated shaft of the trocar, in the various tissue plains of the patient, therefore minimizing the risk of a subcutaneous emphysema.

Yet another object of the present invention is to provide an improved trocar assembly which will effectively seal-off the incision opening about the shaft of the trocar in a safe and effective manner, which is not highly susceptible to puncture or rupture.

Also another object of the present invention is to provide an improved trocar assembly which will not allow air disposed within an internal, inflatable cuff to back-up out of the cuff, thereby leading to its deflation, upon an internal and/or an external pressure being exerted on exposed exterior portions of the cuff.

BRIEF DESCRIPTION OF THE DRAWINGS

For a fuller understanding of the nature of the present invention, reference should be had to the following detailed description taken in connection with the accompanying drawings in which:

FIG. 1 is a perspective view of the trocar assembly of the present invention in use with an instrument operatively disposed therein;

FIG. 2 is a isolated perspective view of the trocar assembly of the present invention;

FIG. 3 is a cross-sectional view of the trocar assembly of the present invention;

FIGS. 4A and B are top cross-sectional views of an embodiment of the locking means of the present invention in an unengaged and an engaged orientation.

FIGS. 29A and 29B illustrate yet another preferred embodiment of the inflatable cuff of the present invention in a detached and attached orientation;

FIGS. 30A and 30B are side cross-sectional views of an embodiment of an upper collar assembly including an adjustable lower contact surface;

FIGS. 31A and 31B are side cross-sectional views of an alternative embodiment of the upper collar assembly including an alternative variable lower contact surface in an unengaged and engaged orientation;

FIG. 32 is a bottom view of embodiment of the variable lower contact surface of the upper collar assembly;

FIG. 33 is a lower view yet of yet another embodiment of the variable lower contact surface of the upper collar assembly of the present invention.

Like reference numerals refer to like parts throughout the several views of the drawings.

DETAILED DESCRIPTION OF THE PREFERRED EMBODIMENT

Figure 5A:
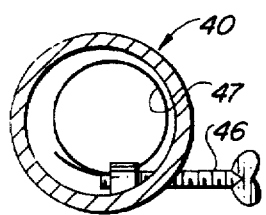
FIGS. 5A and B are top cross-sectional views of another embodiment of the locking means of the present invention in an unengaged and an engaged orientation.
Figure 7A:
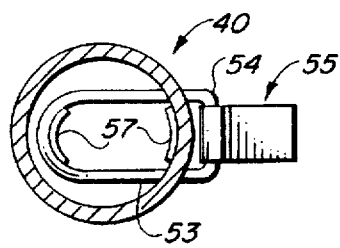
FIGS. 7A and B are top cross-sectional views of another embodiment of the locking means of the present invention in an unengaged and an engaged orientation.

Shown throughout the figures, the present invention is directed towards an improved trocar assembly, generally indicated as 10. Specifically, the trocar assembly 10 will be utilized during laparoscopic and other minimally invasive operative procedures, the most common of which involves some form of abdominal laparoscopic surgery. In use, the trocar assembly 10 forms an incision opening 120 through the various tissue plains 116 in the abdominal wall 115 of a patient. As such, the relatively small diameter of the trocar assembly 10 minimizes the size of the incision opening 120, and in turn minimizes the tissue trauma and recovery necessitated by a patient.

Generally, a plurality of trocar assemblies 10 are used at once and inserted at various locations into the patient. Each of the trocar assemblies 10 therefore provides a conduit through which an operative instrument 100, such as a laparoscopic surgery cutting or grasping instrument, is inserted into the patient. Accordingly, through the use of a visual display, also generally inserted into a patient through a trocar, a doctor is able to perform various procedures within the patient utilizing only a number of small incision openings defined by the trocar assembly 10.

The trocar assembly 10 of the present invention includes primarily an elongate shaft 20. This elongate shaft 20 includes an open proximal end 24, an open distal end 25 and an open axial channel 27 extending therethrough from the proximal end 24 to the distal end 25. In the preferred embodiment, this elongate shaft 20, which is substantially rigid, will be formed of a radiolucent material. Accordingly, through the use of the radiolucent material the elongate shaft 20 will not obscure portions of an internal image of the patient as provided on an X-ray device. Further, the elongate shaft 20 includes a substantially smooth exterior surface 21. The substantially smooth exterior surface 21 of the elongate shaft 20 is structured such that upon piercing insertion of the trocar assembly 10 through the tissue plains 116 of the patient, at the incision opening 120, excess local tissue maceration and traumatization will be prevented. In particular, once the incision opening 120, as defined by a diameter of the elongate shaft 20 is formed, the inward and/or outward sliding of the elongate shaft 20 therethrough will not result in further cutting or scrapping of the exposed tissue plains 116 at the incision opening 120. Additionally, the exposed exterior surface 21 minimizes the resistance encountered during piercing insertion of the trocar assembly 10 into the patient. As such, the risk that excess piercing force will be placed on the trocar assembly 10 during insertion is minimized, and in turn the risk that the trocar assembly 10 will be inserted so far into the patient that it can potentially engage and damage various internal organs is also minimized.

In order to enable the trocar assembly 10 to penetrate the abdominal wall 115 and form the incision opening 120, introduction means are included. In the preferred embodiment the introduction means include a removable piercing member. The piercing member can be in the form of any of a variety of piercing attachments that are inserted through the elongate shaft such that a pointed tip protrudes through the distal end 25 of the elongate shaft 20. This piercing attachment facilitates the initial penetration of the trocar assembly 10 into the patient, and is structured to be removed from the elongate shaft 20 once the trocar assembly 10 has been appropriately introduced into the patient and the necessary incision opening has been formed. Alternatively, however, the introduction means may include one of many types of blunt attachments that extends through the shaft and are structured to facilitate insertion of the trocar assembly 10 through a totally or partially pre-formed incision in the patient in order to fully form and define the incision opening 120 in the patient.

Disposed substantially at the distal end 25 of the elongate shaft 20 is a distal expandable component. The distal expandable component is structured so as to selectively maintain the elongate shaft 20 partially within the patient after the elongate shaft 20 and the distal expandable component have been inserted into the patient. Preferably, the distal expandable component will include at least one inflatable cuff 30. As illustrated in FIGS. 2, 3, 28A and 28B, the inflatable cuff 30 is structured to be selectively disposed between an inflated and an uninflated state within the patient. In particular, when the inflatable cuff 30 is in its uninflated state it is folded up along the exterior surface 21 of the elongate shaft 20 so as to substantially minimize any added insertion diameter of the trocar assembly 10. In this uninflated orientation, the elongate shaft 20 can be easily inserted and removed from the patient. Conversely, when the inflatable cuff 30 is in its inflated orientation, it provides an area of substantially increased diameter about the elongate shaft 20. This area of increased diameter will prevent the elongate shaft 20 from being pulled out of the patient through the precisely sized incision opening 120.

The inflatable cuff 30 is formed of a flexible, yet substantially non-elastic material, such as a canvas, cloth, thin metal or mesh, or a minimally resilient plastic or rubber type material. In particular, the substantially non-elastic material which forms the inflatable cuff 30 is structured such that a thickness of a material wall 31 which comprises the inflatable cuff 30 is uniform along an entire wall surface 31 of the inflatable cuff 30. This uniform wall thickness is maintained both when the cuff is in an uninflated or inflated state, due to the substantially inelastic nature of its material composition, and therefore, especially when the inflatable cuff 30 is in its inflated state, a uniform wall strength will be maintained along the entire wall surface 31 of the inflatable cuff 30. Also, no added tension is placed on the inflatable cuff 30 as a result of its inflation. Accordingly, the risk that the inflatable cuff 30 will rupture during operation is significantly minimized during use. In particular, during use, a variety of counter directional forces are exerted on the inflatable cuff 30. For example, air pressure from within the patient is exerted on the inflatable cuff 30, an outward pulling pressure is exerted on the inflatable cuff 30 upon pulling the trocar assembly 10 in order to clampingly secure it in place, and a lateral pressure is exerted on the inflatable cuff 30 when the trocar assembly 10 is maneuvered into varying angled orientations by a doctor attempting to reach various areas within the patient utilizing the instrument 100 that extends through the trocar assembly 10. Further, because the wall surface 31 of the inflatable cuff 30 is of a uniform thickness and is not under an excessive amount of tension, it will not be easily susceptible to puncture if it is inadvertently contacted by a sharp instrument within the patient.

The inflatable cuff 30, which is structured to seal off the incision opening 120 about the elongate shaft 20 so as to substantially prevent escaping air flow from an interior 119 of the patient through the incision opening 120 around the elongate shaft 20, is structured to be inflated and deflated by way of inflation means. In the preferred embodiment, the inflation means which are structured and disposed to provide for exterior inflation of the inflatable cuff 30 after the inflatable cuff 30 has been inserted into the patient, includes an elongate flow through conduit 33 connected to the inflatable cuff 30. Although the elongate flow through conduit 33 can be separate from the elongate shaft 20, in the preferred embodiment, and so as to minimize a diameter of the trocar assembly 10, the elongate flow through conduit 33 will be formed directly in the wall of the elongate shaft 20. As such, the elongate flow through conduit 33 terminates in an inflatable cuff access 32, that is disposed in fluid flow communication with the inflatable cuff 30, and an exterior end 34, which is positioned near the proximal end 24 of the elongate shaft 20 so as to be accessible after partial insertion of the elongate shaft 20 into the patient. Additionally, valve means are preferably disposed at the exterior end 34 of the flow through conduit 33 so as to prevent air from exiting the inflatable cuff 30 therethrough inadvertently. Specifically, due to the natural tendencies of the air within the inflatable cuff 30, as well as because the added pressure placed on the exterior of the inflatable cuff 30 during various phases of a procedure, the air within the inflatable cuff 30 will seek to escape, thus possibly deflating the inflatable cuff 30 and leading to unwanted release of the trocar assembly 10 from within the patient. Accordingly, the valve means disposed at the exterior end 34 will be structured such that air may be introduced into the inflatable cuff 30 therethrough, and can only be purposefully removed from the inflatable cuff 30 therethrough. Therefore, the valve means may include a one way valve having an exterior release to allow the escape of air only when actuated to allow for removal of the trocar assembly 10. Alternatively, the valve means may include a resilient mass disposed at the exterior end 34 and structured to allow the introduction of air therethrough, such as utilizing a syringe that contains a quantity of air and is inserted into the exterior end 34 of the flow through conduit 33 through the resilient mass to fill the inflatable cuff 30. Evacuation of the air from the inflatable cuff 30 can be similarly achieved using the syringe or some other release mechanism that extends through the mass in order to allow all of the air to escape from the inflatable cuff 30.

As seen in FIGS. 29A and 29B, an alternative embodiment of the distal expandable component incorporates a detachable distal end 25 of the elongate shaft 20. In particular, the detachable distal end 25' includes the inflatable cuff 30 thereon and is structured for threaded engagement on a threaded protrusion 26 that extends from the elongate shaft 20. Further, the threaded protrusion 26 will include an opening 26', corresponding the inflatable cuff access 32 such that upon threaded engagement of the detachable distal end 25' on the threaded protrusion 26, the opening 26' will align itself with the access 32 and allow the necessary airflow therethrough into and out of the inflatable cuff 30. This particular embodiment which utilizes the removable distal end 25' is particularly beneficial to permit effective sterilization of a substantial portion of the trocar assembly 10 while making the detachable distal end 25', which remains within the body during the entire procedure and is generally more difficult to sterilize as a result of the material which forms the inflatable cuff 30, effectively disposable.

Figure 23:
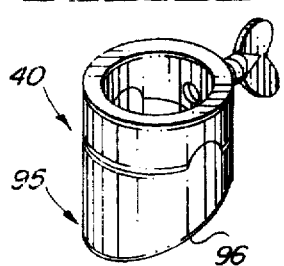
FIG. 23 is a perspective view of an alternative embodiment of the inflatable cuff of the present invention.
Figure 24:
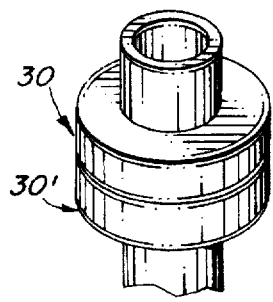
FIG. 24 is an isolated side perspective view of another embodiment of the inflatable cuff of the present invention.
Figure 25:
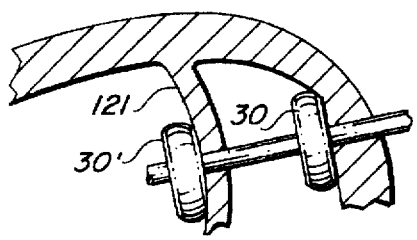
FIG. 25 is a side view of the inflatable cuff of FIG. 24 in operative position within a patient.

Finally, in yet another embodiment of the distal expandable component shown in FIGS. 23-25, two inflatable cuffs 30 and 30' may be disposed at the distal end of the elongate shaft 20. These two inflatable cuffs 30 and 30' may be disposed adjacent one another so as to provide a larger overall cuff, or preferably will be disposed a spaced distance from one another along the elongate shaft 20. Placing two or even more of the inflatable cuffs 30 and 30' along the elongate shaft 20 facilitates operations wherein not only the abdominal wall 115 must be pierced, but also an additional interior tissue wall 121 of the patient must also be pierced. Accordingly, utilizing both inflatable cuffs 30 and 30' the trocar assembly 10 will effectively be maintained to access the appropriate area within the patient and the risk that the distal most portion of the elongate shaft 20 will accidently slip from its passage through the internal tissue wall 121 is eliminated. In this embodiment either a single or two separate inflation means may be incorporated to allow for simultaneous or independent deflation and inflation of the inflatable cuffs 30 and 30'.

Looking now to FIGS. 1, 2 and 4 through 14, the improved trocar assembly 10 of the present invention also includes an upper collar assembly, generally indicated as 40. The upper collar assembly 40 is structured to be slideably disposed on the elongate shaft 20, preferably nearer to the proximal end 24 of the elongate shaft 20. The upper collar assembly 40 is structured to slide down into engaging contact with an upper tissue layer 117 of the tissue wall 115 through which the trocar assembly 10 is inserted so as to essentially sandwich the tissue wall 115 between the upper collar assembly 40 and the distal expandable component which abuts an internal surface 118 of the tissue wall 115. Accordingly, in order top enable the upper collar assembly 40 to be secured at a desired relative position along the substantially smooth exterior surface 21 of the elongate shaft 20, the upper collar assembly 40 includes locking means. These locking means are structured to securely and non-slideably engage the elongate shaft 20, thereby securing the upper collar assembly 40 in place. Therefore, in use, the elongate shaft 20 of the trocar assembly 10 is inserted into the patient until the distal end 25 of the elongate shaft 20 and the inflatable cuff 30 thereon pass beyond the interior surface 118 of the tissue wall 115 being pierced. At that point, the inflatable cuff 30 is inflated and the trocar assembly 10 is pulled outward until the inflatable cuff 30 abuts the interior surface 118 of the tissue wall 115. Next, the upper collar assembly 40 is pushed downwardly until it firmly engages the upper tissue layer 117 of the tissue wall 115 and clamps the tissue wall 115 in place. Utilizing the locking means the upper collar assembly 40 is then secured in the desired position thereby ensuring that the elongate shaft 20 of the trocar assembly 10 is maintained in a substantially secure and stable orientation in the incision opening 120 of the patient for the duration of an operational procedure.

Although any locking means which will effectively secure the upper collar assembly 40 in place along the smooth elongate shaft 20 may be utilized, hereafter a number of preferred locking means are recited and illustrated throughout the figures. In a first series of embodiments of the upper collar assembly 40, the locking means includes an interior clamping member disposed within the upper collar assembly 40 and structured to be exteriorly actuated so as to clampingly, securely and non-slidably engage the elongate shaft 20 therein. As illustrated in FIGS. 4A and 4B, the interior clamping member may include a threaded screw 42 having a clamping face 43. In use, the exteriorly exposed threaded screw 42 is turned so as to urge the clamping face 43 towards the elongate shaft 20 until the elongate shaft 20 is pinned between the clamping face 43 and an interior 41 of the upper collar assembly 40. Further, so as to prevent slippage, a resilient or other type non-stick interior surface 44 may be included so as to provide a substantial grip on the elongate shaft 20.

Figure 5B:
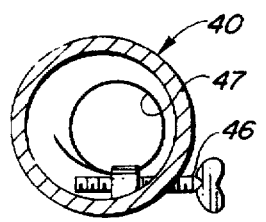
Figure 7B:
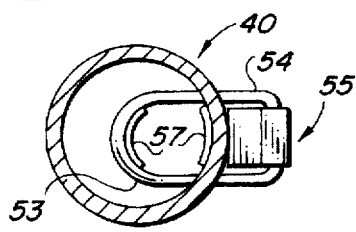
FIGS. 7C and 7D are side cross-sectional views further illustrating the unengaged and engaged orientations of FIGS. 7A and 7B, respectively.

Alternatively, as in FIGS. 5A and 5B, the interior clamping member may include a clamp ring 47 which extends about the elongate shaft 20. In use, an exteriorly exposed screw 46 is turned so as to reduce an inner diameter of the clamp ring 47 that rides thereon so as to secure the clamp ring 47 about the elongate shaft 20.

Further, as illustrated in FIGS. 7A through 7D, a sliding clamp member 53 having an exteriorly exposed end 54 may be utilized to grasp the elongate shaft 20. In use, the clamp member 53 is pulled out of the upper collar assembly 40 by the actuation of an exterior pivot pin 55. The exterior pivot pin 55 includes an increased width portion 56 and is structured to be pivotally actuated until the clamp ring 53 is pulled sufficiently out of the upper collar assembly 40 such that it clampingly hold the elongate shaft 20 against an interior surface of the upper collar assembly 40. Additionally, an opposing gripping surfaces 57 may be included to increase the strength of the grip and prevent accidental slippage of the elongate shaft 20.

Figure 8A:
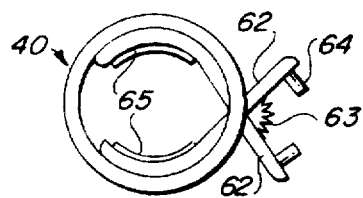
FIGS. 8A and 8B are top cross-sectional views of another embodiment of the locking means of the present invention in an unengaged and an engaged orientation.
Figure 8B:
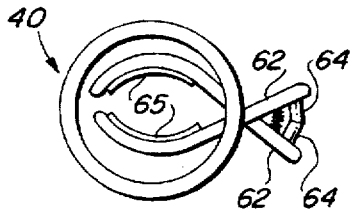

Also, the interior clamping member, as in FIGS. 8A and 8B, may include a pair of opposing clamp arms 59 and 60 which extend into the upper collar assembly 40. Specifically, the clamp arms 59 and 60 are normally held in a spaced, expanded position by an exterior biasing means such as a spring 63. When the desired position of the upper collar assembly 40 is attained, the protruding handle portions 61 and 62 of the clamp arms 59 and 60 are pushed towards one another until a pair of stepped tracks 64, one being disposed on of each of the members 61 and 62, engage one another in a racheted manner in order to maintain the relative clamping position of the clamp arms 59 and 60. In this regard, the grip of the clamp arms 59 and 60 can be easily increased by pushing the members 61 and 62 towards one another, however, the stepped tracks 64 must be pulled separate from one another in order to enable the spring 63 to return the clamp arms 59 and 60 to their normal open position. Further, an interior non-sliding, grip increasing surface 65 can be included.

Figure 9A:
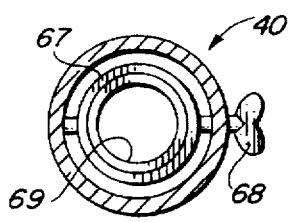
FIGS. 9A and 9B are top cross-sectional views of another embodiment of the locking means of the present invention in an unengaged and an engaged orientation.
Figure 9B:
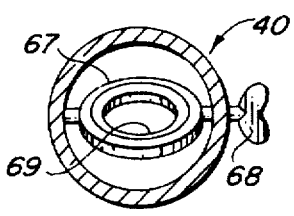

As yet another embodiment of the interior clamping member, shown in FIGS. 9A and 9B, a resilient clamp ring 67 is included and tightened by way of an exterior pin 68. Specifically as the exterior pin 68 is rotated within the upper collar assembly 40 the resilient clamp ring 67 which is secured thereto and is pivotally suspended on opposite sides thereof within the upper collar assembly, also rotates, thereby effectively reducing an axial cross-sectional diameter which securely engages the elongate shaft 20. As with the other embodiments an interior non-slip, grip increasing surface 69 is preferably also included.

Figure 14:
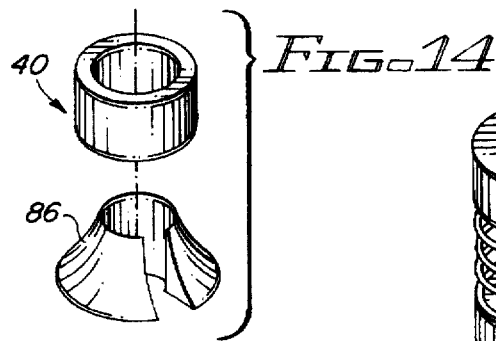
FIG. 14 is an isolated perspective view of yet another embodiment of the upper collar assembly of the present invention.

Finally, as detailed in FIG. 14, an outwardly flanged clamping member 86 may be included, the upper collar assembly 40 being structured to slide down over the outwardly flanged clamping member 86 so as to reduce its internal diameter and clamp the elongate shaft 20 within the outwardly flanged clamping member 86. It should be noted that the preceding examples are merely some of the preferred interior clamping members to be utilized and implemented within the scope of the present invention.

Figure 11A:
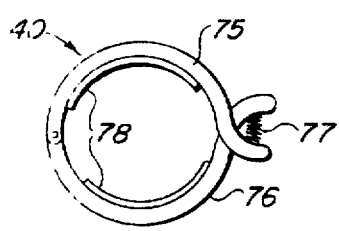
FIGS. 11A and 11B are top cross-sectional views of another embodiment of the locking means of the present invention in an unengaged and an engaged orientation.
Figure 11B:
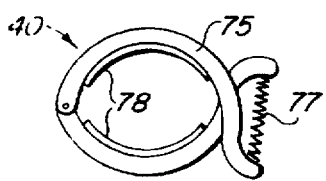

In another alternative embodiment, the locking means will include tightening means structured and disposed to adjustably vary an interior diameter of the upper collar assembly 40 itself, so as to enable the upper collar assembly 40 to clampingly, securely and non-slideably engage the elongate shaft 20. Turning to FIGS. 11A and 11B, the tightening means may include a biasing spring 77 disposed between two opposing arms 75 and 76 which comprise the upper collar assembly. In use, the spring 77 will preferably maintain the arms 75 and 76 urged towards one another to provide a reduced diameter of the upper collar assembly 40. Accordingly, when adjustment of the upper collar assembly 40 is necessitated along the elongate shaft 20, the biasing spring 77 must be compressed, thereby increasing the internal diameter of the upper collar assembly 40 and facilitating slided movement thereof, until the appropriate orientation of the upper collar assembly 40 is achieved. Similarly, an interior non-sliding, grip increasing surface 78 may be incorporated.

Figure 12A:
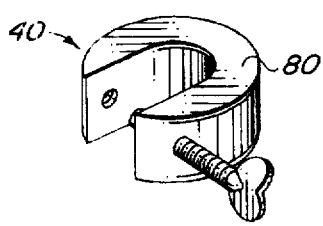
FIGS. 12A and 12B are top cross-sectional views of another embodiment of the locking means of the present invention in an unengaged and an engaged orientation.
Figure 12B:
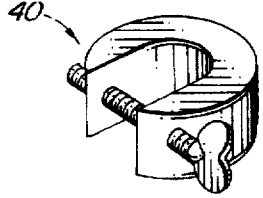

Alternatively, as in FIGS. 12A and 12B the upper collar assembly 40 includes a generally C-shape 80 wherein the elongate shaft 20 is received. By screwing a preferably threaded tightening member 81 through the upper collar assembly 40, the interior diameter of the general C-shaped upper collar assembly 80 is reduced to provide for appropriate clamped gripping of the elongate shaft 20.

Figures 13A, 13B:
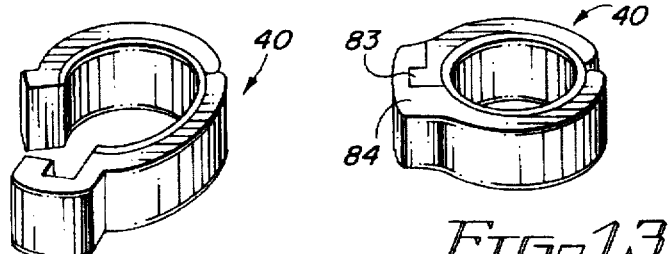
FIGS. 13A and 13B are top cross-sectional views of another embodiment of the locking means of the present invention in an unengaged and an engaged orientation.

In yet another embodiment of the upper collar assembly 40, a pair of opposing snap fitting edges 83 and 84, as in FIGS. 13A and 13B, may be included to be snapped fitted with one another and accordingly reduce the interior diameter of the upper collar assembly 40. As such, the snap fitting edges 83 and 84 are disengaged when the upper collar assembly 40 is to be moved along the elongate shaft 20, and when the appropriate position is achieved the edges 83 and 84 are snap fitted with one another to maintain the proper fitted disposition about the elongate shaft 20.

Figure 10A:
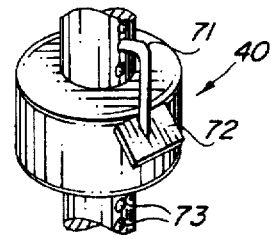
FIGS. 10A and 10B are top cross-sectional views of another embodiment of the locking means of the present invention in an unengaged and an engaged orientation.
Figure 10B:
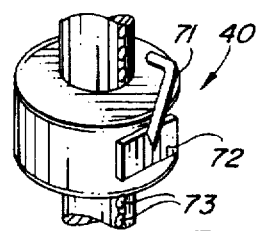

Also, as detailed in FIGS. 10A and 10B, a plurality of small recess 73 may be formed along a length of the elongate shaft 20 such that an actuatable lock pin 71 can be inserted therein to secure the upper collar assembly 40 in a desired orientation along the elongate shaft 20. The actuatable lock pin 71 is exteriorly actuatable by a pivot lever 72 which removes the actuatable lock pin 71 from an engaged position within one of the recess 73 for adjustable positioning of the upper collar assembly 40, and allows the actuatable lock pin 71 to return to its normal, engaging position upon release of the lever 72. In this embodiment, the recesses 73 are preferably tapered and/or finished such that they will not substantially diminish the smooth exterior surface 21 of the elongate shaft 20 and will accordingly not engage the interior tissue plains 115 so as to cause additional tissue traumatization.

Figure 6A:
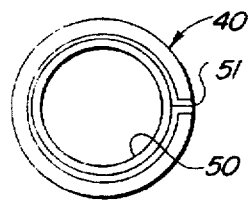
FIGS. 6A and B are top cross-sectional views of another embodiment of the locking means of the present invention in an unengaged and an engaged orientation.
Figure 7C:
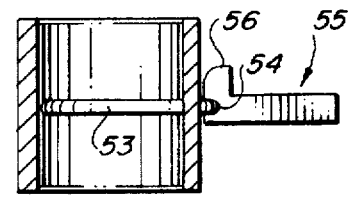
Figure 6B:
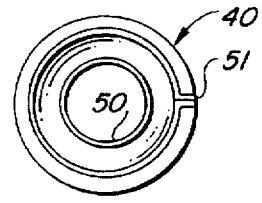
Figure 7D:
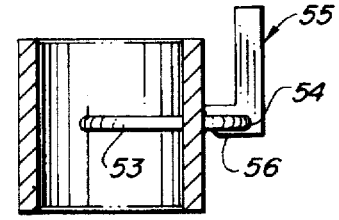

As in FIGS. 6A and 6B, an inflatable interior clamping bladder 50 may be incorporated into the locking means. The clamping bladder 50 is structured to be inflated through an air inlet 51 so as to reduce an interior diameter thereof and effectively clamp the elongate shaft 20 therein.

As previously stated, these further preferred embodiments of the locking means of the upper collar assembly 40 should not be construed as exhaustive of the variety of efficient and effective locking means, so long as the locking means will effectively provide for grip securing of the upper collar assembly without necessitating that the generally smooth exterior surface 21 of the elongate shaft 20 be altered.

Figure 15:
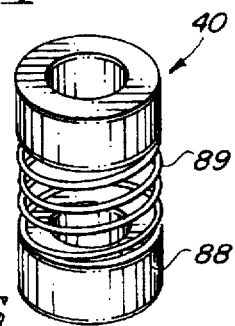
FIG. 15 is an isolated side perspective view of an alternative embodiment of the upper collar assembly of the present invention.
Figure 17:
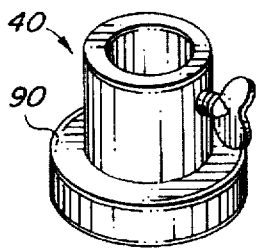
FIG. 17 is an isolated side perspective view of the upper collar assembly of the present invention.
Figure 16:
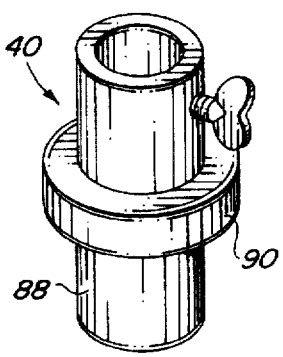
FIG. 16 is an isolated side perspective view of an alternative embodiment of the upper collar assembly of the present invention.

So as to ensure that the abdominal wall 115 is firmly and fixedly clamped between the upper collar assembly 40 and the inflatable cuff 30, a generally firm downward clamping force is applied on the upper collar assembly 40 before it is secured in place along the elongate shaft 20. As such, it is preferred that the downward clamping of the upper collar assembly 40 does not traumatize or damage the upper tissue layer 117 of the tissue wall 115. Accordingly, in an embodiment of the present invention the upper collar assembly 40 will include a resilient spacer disposed between a main body of the upper collar assembly 40 and a lower contact segment 88 of the upper collar assembly 40, which actually engages the tissue wall 115. Turning to FIGS. 15 through 17, the resilient spacer may include biasing means such as spring 89, or an inflatable bladder 90 disposed between the main body and the lower contact segment 88. Accordingly, the downward forces exerted at the upper collar assembly 40 will be evenly distributed along an entire surface of the lower contact segment 88 so as to minimize the potentially harmful effects to the tissue wall 115 at a particular high pressure point of the upper collar assembly 40. Similarly, the inflatable bladder 90 may also be directly utilized as the lower contact segment and will directly rest atop the tissue wall 115 and provide evenly distributed downward pressure thereon. Additionally, in the preferred embodiment it is also important that after the upper collar assembly 40 engages the tissue wall 115, the incision opening 120 around the elongate shaft 20 is not blocked off. In particular, if some air inadvertently seeps past the inflatable cuff 30, is important that this air not be trapped in the various tissue plains 116 within the patient because such trapped air can lead to subcutaneous emphysema. Therefore, it is preferred that any air which does manage to escape from the interior of the patient will completely exit the body and not be hindered by the upper collar assembly 40. In this regard, the upper collar assembly 40 will preferably not seal off the entire incision opening 120 or will include one or a plurality of passages or openings to allow the free release of air should any escape.

During the minimally invasive procedures which employ a trocar assembly 10, a physician must reach a variety of locations within the patient through the single incision opening. Accordingly, and due to the orientation of the tissue wall 115 through which the incision opening is made, the precise orientation of the trocar assembly 10 and instrument 110 that passes therethrough subsequent to insertion may not be optimal. This necessitates that a physician must often angle or maneuver the trocar assembly 10 and instrument 110 within the patient so as to reach the desired locations. Alternatively, however, in some circumstances it is preferred that a specific orientation of the trocar assembly 10 and the instrument 110 contained therein be specifically maintained such that accidental pivoting or moving thereof is eliminated. For this reason, the upper collar assembly 40 of the trocar assembly 10 of the present invention is equipped with a specifically adapted or a variable lower contact surface. This lower contact surface can be varied by replacing the upper collar assembly 40 to correspond the necessary use, by including extra attachments to adapt the upper collar assembly 40, or by maintaining a variety of individual trocar assemblies 10, each having a specific, desired lower contact surface corresponding a specific need.

Figure 18:
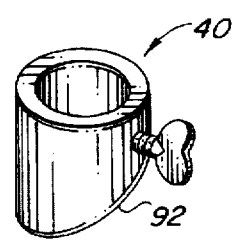
FIG. 18 is an isolated side perspective view of another embodiment of the upper collar assembly of the present invention.

Turning first to FIG. 18, in one embodiment of the upper collar assembly 40, an angled lower contact surface 92 is included. The angle lower contact surface 92 facilitates maintenance of the trocar assembly 10 in a specific desired angled orientation for use in situations where the incision opening 120 cannot be made directly over the area in which a procedure is being performed.

Figure 19:
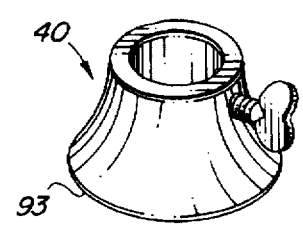
FIG. 19 is an isolated side perspective view of another embodiment of the upper collar assembly of the present invention.

Alternatively, as detailed in FIG. 19, an outwardly flanged lower contact surface 93 may be included. This outwardly flanged lower contact surface 93 will maintain the elongate shaft of the trocar assembly 10 disposed in a substantially perpendicular orientation, relative to a plain of an exterior tissue surface 117, thereby maintaining the trocar assembly 10 properly oriented if it must be left unattended momentarily or if it must otherwise be left to remain in a specific, desired orientation.

Figure 20:
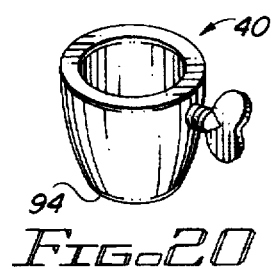
FIG. 20 is an isolated side perspective view of another embodiment of the upper collar assembly of the present invention.

Further, as in FIG. 20, a rounded lower contact surface 94 may be included on the upper collar assembly 40. This rounded lower contact surface 94 is of particular importance when the procedure to be performed requires substantial maneuvering of the operative instrument 110 within the patient. By providing the rounded lower contact surface 94, the elongate shaft 20 can be easily pivoted and reoriented to facilitate internal maneuvering.

Figure 21:
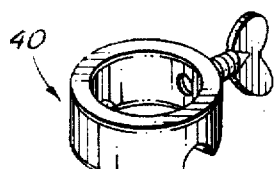
FIG. 21 is an isolated, partially exploited view of an embodiment of the upper collar assembly of the present invention.
Figure 22:
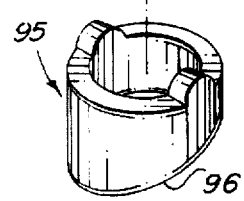
FIG. 22 is an isolated side perspective view of the embodiment of FIG. 21 in an engaged orientation.

All of the various lower contact surfaces, as well as any additional configurations which may be appropriate, can either be build directly onto the upper collar assembly 40, or alternatively as illustrated in FIGS. 21 and 22 may be incorporated as an add-on segment 95 which includes the specific desired lower contact surface 96. As such, in use, depending on the particular orientation needs for the specific trocar assembly 10 being utilized, the appropriate replaceable lower contact surface member 95 may be installed and engaged with the main body of the upper collar assembly 40.

Looking to FIGS. 30 through 33, some surgical situations require that the orientation of the elongate shaft 20 of the trocar assembly 10 be varied throughout a procedure, but that each new orientation be stably maintained. Accordingly, the device of the present invention may include a variably positionable lower contact surface to maintain the elongate shaft 20 normally in one predetermined desired orientation, while allowing the orientation to be varied into a desired angled orientation. Preferably, this will include elevation means positionable between a retracted, in the upper collar assembly, and an extended position. As in FIGS. 30A and 30B, the elevation means may include a rigid, retractable pivot member 97 may be included within the upper collar assembly 40 this retractable pivot member 97, which is preferably exteriorly actuatable via a lever 98, is structured to remain retracted within the upper collar assembly 40 when not needed such that the orientation of the elongate shaft 20 will be dictated by the normal lower surface of the upper collar assembly 40. When, however, a specific different orientation, and preferably an angled orientation, is required, the retractable pivot member 97 is pushed out from within the upper collar assembly 40 so as to appropriately tilt the upper collar assembly 40, and the elongate shaft 20, to the desired angled orientation. The retractable pivot member 97 can be structured to have two or a number of finite tilted orientations.

Similarly, the elevation member in the upper collar assembly 40 can be achieved with an inflatable angling member 99 as in FIGS. 31A and 31B. The inflatable angling member 99 is normally uninflated, but when inflated through an inflation inlet 100 will function to appropriately angle the trocar assembly 10 as desired. As such, the quantity of air that is inserted into the inflatable angling member 99 will determine the degree of tilting provided.

Finally, to provide for more facilitated varying of the lower contact surface during a procedure, the preferred embodiments of Figures of 32 and 33 may also be incorporated into the upper collar assembly 40. Specifically, the upper collar assembly 40 will preferably include at least two opposing, interconnecting bladders disposed in fluid flow communication with one another. In a first preferred embodiment shown in FIG. 32, both interconnecting bladders 101 and 102 are formed of an elastic material, with a first of the two bladders 101 having a greater, relaxed cross-sectional diameter than a second of the two bladders 102. As such, and based upon LaPlace's laws of physics, the fluid contained within the bladders will tend to remain within the first of the bladders 101 providing an appropriate angled orientation for the trocar assembly 10 in accordance therewith. When, however, a physician wishes to tilt the orientation by pivoting the angle of the trocar assembly 10, a quantity of pressure is applied to the first bladder 101 such that some of the fluid will exit the first bladder 101 and flow into the second bladder 102, thus permitting temporary pivotal repositioning. The pivoted positioning is temporary because when the pivoting force of the trocar assembly 10 on the first bladder 101 is released by the physician, the fluid will return to the first bladder 101 and the trocar assembly 10 will return to its normal, original, angled orientation as defined by the first bladder 101.

Similarly, an additional preferred embodiment of FIG. 33 includes a first bladder 101 formed of the elastic material and a second bladder 103 formed of an in-elastic material. As such, due to the natural compression force of the elastic material 101, the fluid contained in the bladders will tend to remain in the inelastic material, second bladder 103, such that the second bladder 103 provides the normal angled orientation. This orientation is maintained until a downward pivoting force is exerted on the second bladder 103 so as to urge some of the fluid therefrom into the first, elastic bladder 101. Accordingly, the necessary angled orientation for the trocar assembly 10 can be maintained at all times while allowing a physician quick and easy maneuverability should it become necessary during an operational procedure.

Figure 27:
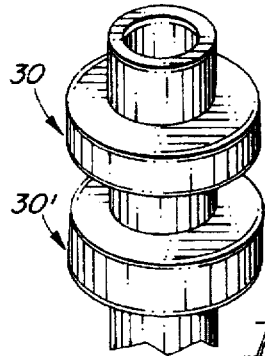
FIG. 27 is a side perspective view of an alternative embodiment of the instrument stabilization means of the present invention.
Figure 26A:
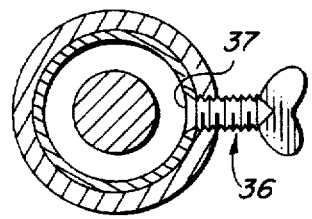
FIGS. 26A and 26B are top cross-sectional views of the instrument stabilization means of the present invention.
Figure 26B:
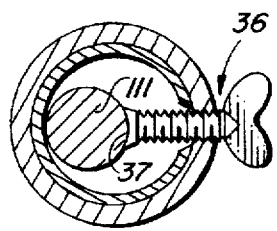
Figure 28A:
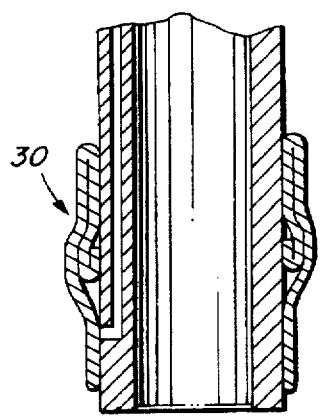
FIGS. 28A and 28B are side cross sectional views of a preferred embodiment of the inflatable cuff of the present invention in an uninflated and inflated orientation.
Figure 28B:
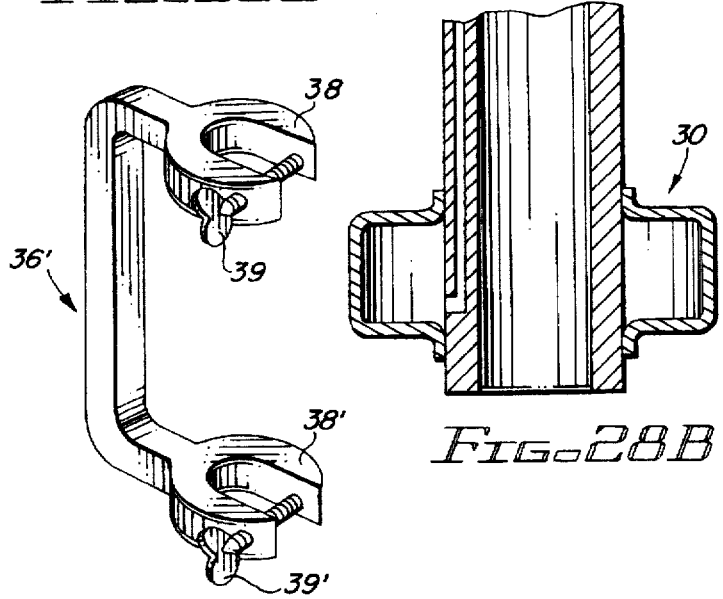

Further, to provide a physician with greater efficiency and freedom within the operating environment, a preferred environment of the trocar assembly 10 of the present invention, as illustrated in FIGS. 1, 26 and 27, will include instrument stabilization means. Specifically the instrument stabilization means will be structured and disposed to maintain a laparoscopic instrument 110, which has been inserted into the patient through the elongate shaft 20, to be securely and non-slideably maintained in a select position and orientation within the elongate shaft 20. In particular, during various operating procedures a laparoscopic instrument 110 is utilized merely for grasping, clamping or retracting type purposes that may not need constant attention. Conventional operational procedures, however, require that a physician or physician's assistant constantly hold the laparoscopic instrument 110, or otherwise secure the laparoscopic instrument 110 to some fixed object in the operating room. Often this securing of the laparoscopic instrument 110 to some fixed object can incorporate a hazardous and/or make-shift mechanism that is susceptible to accidental release. In order to eliminate this hazard, the instrument stabilization means are incorporated directly into the trocar assembly 10. In the preferred embodiment, a clamping screw 36, with an interior clamping surface 37, as in FIGS. 26A and 26B, is utilized. As the clamping screw 36 is rotated and inserted into the elongate shaft 20, it clamps the laparoscopic instrument 110 against an interior of the elongate shaft 20, thereby maintaining it fixedly in place and preventing it from sliding into or out of the patient when unattended. Alternatively, as in FIG. 27, the instrument stabilization means 36' can include a pair of opposed grasper members 38 and 38' that are secured to one another, and each of which is respectively secured to the elongate shaft 20 of the trocar assembly 10 and the shaft 111 of the laparoscopic instrument 110. Although any of a variety means can be implemented to secure the opposed grasper members 38 and 38' to one another, a pair of tightening screws 39 and 39' are preferably incorporated to maintain the secure fastening of the instrument stabilization means 36' to the trocar assembly 10 and the instrument 110.

As with most conventional trocar assemblies, the trocar assembly 10 may also include a variety of added features. For example, the trocar assembly 10 will preferably include a flap valve to prevent leaks of the pneumoperitoneum both when an instrument is in the shaft and when no instrument is in the shaft. Further, another common element includes an air inlet below the flap valve for the purpose of maintaining the pneumoperitoneum.

While this invention has been shown and described in what is considered to be a practical and preferred embodiment, it is recognized that departures may be made within the spirit and scope of this invention which should, therefore, not be limited except as set forth in the claims which follow and within the doctrine of equivalents.

Now that the invention has been described,

What is claimed:

1. An improved laparoscopy trocar assembly comprising:
   an elongate shaft, said elongate shaft including an open proximal end, an open distal end, and an axial channel extending from said distal end to said proximal end,
   said elongate shaft including a substantially smooth exterior surface so as to prevent frictional engagement of said exterior surface with various tissue planes at an incision opening, thereby reducing a force required to insert said shaft into a patient and substantially minimizing local tissue maceration and traumatization at the tissue planes,
   a distal expandable component disposed substantially at said distal end of said elongate shaft and structured to selectively maintain said elongate shaft partially within the patient subsequent to insertion of said distal end of said shaft and said distal expandable component into the patient,
   said distal expandable component including at least one inflatable cuff, said inflatable cuff being structured to be selectively disposed in an inflated and an uninflated state within the patient, said inflatable cuff being formed of a flexible, substantially non-elastic material such that a wall thickness of said inflatable cuff is uniform along an entire surface thereof both when said cuff is in said inflated and uninflated states, thereby substantially reducing a likelihood that said inflatable cuff will rupture, said inflatable cuff sealing off the incision opening about said elongate shaft so as to substantially prevent air flow from an interior of the patient through said incision opening, inflation means structured and disposed to provide for exterior inflation of said inflatable cuff once said inflatable cuff is disposed within the patient, an upper collar assembly slidably disposed on said elongate shaft substantially at said proximal end thereof, said upper collar assembly including locking means structured to engage said elongate shaft and non-slidably secure said collar assembly at a relative position along said substantially smooth exterior surface of said elongate shaft so as to substantially captivate various tissue planes of the patient, which have been pierced by said elongate shaft, between said upper collar assembly and said inflatable cuff, in said inflated state, and thereby maintain said elongate shaft substantially securely and stably disposed in the incision opening of the patient, said wherein upper collar assembly permits air which does seek to exit the patient from the incision opening about said exterior surface of said elongate shaft to completely exit the patient and thereby not leak from the patient into the various tissue planes leading to subcutaneous emphysema when said upper collar assembly and said inflatable cuff captivate said tissue planes, and introduction means structured and disposed to facilitate passage of said elongate shaft through the various tissue planes of the patient so as to define the incision opening.

2. An improved laparoscopy trocar assembly as recited in claim 1 wherein said inflation means includes an elongate flow through conduit extending through said elongate shaft from said proximal end thereof into fluid flow communication with said inflatable cuff so as to allow exterior inflation of said inflatable cuff therethrough.

3. An improved laparoscopy trocar assembly as recited in claim 2 wherein said flow through conduit includes valve means disposed at an exterior end thereof structured and disposed to prevent air from exiting said inflatable cuff therethrough inadvertently.

4. An improved laparoscopy trocar assembly as recited in claim 3 wherein said valve means are structured to facilitate insertion of a syringe therethrough for introduction of air into said elongate flow through conduit and inflation of said inflatable cuff.

5. An improved laparoscopy trocar assembly as recited in claim 1 further including instrument stabilization means on said elongate shaft structured and disposed to maintain a laproscopic instrument, which is inserted into the patient through said axial channel, securely and non-slidably disposed in a select, variable position and orientation within said elongate shaft.

6. An improved laparoscopy trocar assembly as recited in claim 1 wherein said elongate shaft is formed of a substantially radiolucent material.

7. An improved laparoscopy trocar assembly as recited in claim 1 wherein said locking means includes tightening means extending transversely structured and disposed to adjustably vary an interior diameter of said upper collar assembly so as to enable said upper collar assembly to clampingly, securely and non-slidingly engage said elongate shaft.

8. An improved laparoscopy trocar assembly as recited in claim 1 wherein said distal expandable component is removable from said elongate shaft so as to facilitate independent sterilization of said elongate shaft.

9. An improved laparoscopy trocar assembly comprising:

an elongate shaft, said elongate shaft including an open proximal end, an open distal end, and an axial channel extending from said distal end to said proximal end, a distal expandable component disposed substantially at said distal end of said elongate shaft and structured to selectively maintain said elongate shaft partially within a patient subsequent to insertion of said distal end of said shaft and said distal expandable component into the patient, said distal expandable component including at least one inflatable cuff, said inflatable cuff being structured to be selectively disposed in an inflated and an uninflated state within the patient, said inflatable cuff being formed of a flexible, substantially non-elastic material such that a wall thickness of said inflatable cuff is uniform along an entire surface thereof both when said cuff is in said inflated and uninflated states, thereby substantially reducing a likelihood that said inflatable cuff will rupture, said inflatable cuff sealing off a incision opening about said elongate shaft so as to substantially prevent air flow from an interior of the patient through said incision opening, inflation means structured and disposed to provide for exterior inflation of said inflatable cuff once said inflatable cuff is disposed within the patient, an upper collar assembly slidably disposed on said elongate shaft substantially at said proximal end thereof, said upper collar assembly including locking means structured to engage said elongate shaft and non-slidably secure said collar assembly at a relative position along a substantially smooth exterior surface of said elongate shaft so as to substantially captivate various tissue planes of the patient, which have been pierced by said elongate shaft, between said upper collar assembly and said inflatable cuff, in said inflated state, and thereby maintain said elongate shaft substantially securely and stably disposed in the incision opening of the patient, said wherein upper collar assembly permits air which does seek to exit the patient from the incision opening about said exterior surface of said elongate shaft to completely exit the patient and thereby not leak from the patient into the various tissue planes leading to subcutaneous emphysema when said upper collar assembly and said inflatable cuff captivate said tissue planes, and introduction means structured and disposed to facilitate passage of said elongate shaft through the various tissue planes of the patient so as to define the incision opening.

10. An improved laparoscopy trocar assembly comprising:

an elongate shaft, said elongate shaft including an open proximal end, an open distal end, and an axial channel extending from said distal end to said proximal end, a distal expandable component disposed substantially at said distal end of said elongate shaft and structured to selectively maintain said elongate shaft partially within a patient subsequent to insertion of said distal end of said shaft and said distal expandable component into the patient, said distal expandable component including at least one inflatable cuff, said inflatable cuff being structured to be selectively disposed in an inflated and an uninflated state within the patient, said inflatable cuff sealing off an incision opening about said elongate shaft so as to substantially prevent air flow from an interior of the patient through said incision opening, inflation means structured and disposed to provide for exterior inflation of said inflatable cuff once said inflatable cuff is disposed within the patient, an upper collar assembly slidably disposed on said elongate shaft substantially at said proximal end thereof, said upper collar assembly including locking means structured to engage said elongate shaft and non-slidably secure said collar assembly at a relative position along a substantially smooth exterior surface of said elongate shaft so as to substantially captivate various tissue planes of the patient, which have been pierced by said elongate shaft, between said upper collar assembly and said inflatable cuff, in said inflated state, and thereby maintain said elongate shaft substantially securely and stably disposed in the incision opening of the patient, an engagement face of said collar assembly which contacts the patient having an angular orientation greater than 50 degrees from a central axis of elongate shaft so as to contact the patient without wedging into the incision opening, thereby minimizing an enlargement of the incision opening and minimizing a risk that air which does seek to exit the patient from the incision opening about said exterior surface of said elongate shaft will not completely exit the patient and will leak from the patient into the various tissue planes leading to subcutaneous emphysema, and introduction means structured and disposed to facilitate passage of said elongate shaft through the various tissue planes of the patient so as to define the incision opening.

11. An improved laparoscopy trocar assembly comprising:

an elongate shaft, said elongate shaft including an open proximal end, an open distal end, and an axial channel extending from said distal end to said proximal end, a distal expandable component disposed substantially at said distal end of said elongate shaft and structured to selectively maintain said elongate shaft partially within the patient subsequent to insertion of said distal end of said shaft and said distal expandable component into the patient, said distal expandable component including at least one inflatable cuff, said inflatable cuff being structured to be selectively disposed in an inflated and an uninflated state within the patient, said inflatable cuff sealing off an incision opening about said elongate shaft so as to substantially prevent air flow from an interior of the patient through said incision opening, inflation means structured and disposed to provide for exterior inflation of said inflatable cuff once said inflatable cuff is disposed within the patient, an upper collar assembly slidably disposed on said elongate shaft substantially at said proximal end thereof, said upper collar assembly including locking means structured to engage said elongate shaft and non-slidably secure said collar assembly at a relative position along a substantially smooth exterior surface of said elongate shaft so as to substantially captivate various tissue planes of the patient, which have been pierced by said elongate shaft, between said upper collar assembly and said inflatable cuff, in said inflated state, and thereby maintain said elongate shaft substantially securely and stably disposed in the incision opening of the patient, introduction means structured and disposed to facilitate passage of said elongate shaft through the various tissue planes of the patient so as to define the incision opening, and instrument stabilization means on said elongate for maintaining a laparoscopic instrument, which is inserted into the patient through said axial channel, securely and non-slidably disposed in a select, variable position and orientation within said elongate shaft.

* * * * *